United States Patent [19]

Goralski

[11] 4,309,554

[45] Jan. 5, 1982

[54] 3-(2-THIOPHENESULFONYL)-2-HALO-PROPANENITRILES

[75] Inventor: Christian T. Goralski, Midland, Mich.

[73] Assignee: The Dow Chemical Company, Midland, Mich.

[21] Appl. No.: 144,485

[22] Filed: Apr. 28, 1980

[51] Int. Cl.³ .............................................. C07D 333/34
[52] U.S. Cl. ......................................... 549/62; 424/275
[58] Field of Search ........................................... 549/62

[56] References Cited

U.S. PATENT DOCUMENTS 3,238,094  3/1966  Heininger et al. ................... 424/304
3,541,119  11/1970  Richter et al. ..................... 549/62 X
3,903,298  9/1975  Smith et al. ......................... 424/303

Primary Examiner—John D. Randolph

[57] ABSTRACT

3-(2-Thiophenesulfonyl)-2-halopropanenitriles of the formula

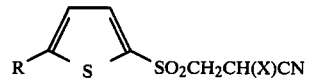

wherein R is H, $C_{1-4}$ alkyl, Br or Cl and X is Br or Cl. The compounds have antimicrobial utility.

5 Claims, No Drawings

3-(2-THIOPHENESULFONYL)-2-HALO-PROPANENITRILES

DESCRIPTION OF THE PRIOR ART

U.S. Pat. No. 3,238,094 discloses phenylsulfonyl haloalkanenitriles wherein the phenyl group may be substituted and the haloalkanenitriles are halopropionitriles, halo being chloro or bromo. The compounds are said to be bactericidal and fungicidal. U.S. Pat. No. 3,903,298 discloses compounds of the formula $RSO_3CH_2CN$ where R is said to be phenyl, substituted phenyl, thienyl or substituted thienyl. The sole thienyl compound actually disclosed is cyanomethyl 2-thiophenesulfonate. The compounds are said to inhibit plant pathogenic bacteria and fungi.

SUMMARY OF THE INVENTION

This invention concerns 3-(2-thiophenesulfonyl)-2-halopropanenitriles represented by the formula

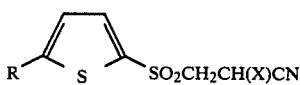

wherein R is H, $C_{1-4}$ alkyl, Br or Cl and X is Br or Cl. The compounds have antimicrobial utility. The compounds are adducts of a thiophenesulfonyl halide and acrylonitrile.

The compounds are prepared by reacting a 2-thiophenesulfonyl chloride or bromide with acrylonitrile in the presence of acetonitrile, anhydrous cupric chloride or bromide and a tri-(lower alkyl) amine hydrochloride or hydrobromide, advantageously by freezing the mixture, evacuating the vessel containing the mixture and heating the sealed mixture in an oil bath at about 115° C. until reaction is substantially complete, usually within about 24 hours. After cooling, the seal of the reaction container is broken and the contents transferred to a vessel, the volatiles are removed in vacuo and a residual heavy oil product is recovered. It is mixed with a small amount of lower alkanol, advantageously methanol, and the resulting solution is cooled to give crude product. The crude product is recrystallized from absolute ethanol to give purified product as small plates. In the reaction, a substantial excess of acrylonitrile is used, usually about 2 molar proportions per molar proportion of the 2-thiophenesulfonyl halide. The primary reactant may be either a 2-thiophenesulfonyl chloride or bromide. When the chloride is used, then a tri-(lower alkyl) amine hydrochloride and cupric chloride are used in the reaction mixture, and when the sulfonyl bromide is used as primary reactant, then a tri-(lower alkyl) amine hydrobromide and cupric bromide are used in the reaction mixture.

The compounds have antimicrobial utility. In conventional in vitro agar Petri dish dilution tests for determining antimicrobial activity, the compounds of the Examples had minimum inhibitory concentrations (MIC) against the indicated organisms in parts per million (ppm) as follows:

TABLE I

| Compound of Example | MIC, ppm | | | | | | | | | | | | |
|---|---|---|---|---|---|---|---|---|---|---|---|---|---|
| | Sa* | Ec | Ca | Tm | An | Be | Aa | Cp | Pp | St | Ps 10 | Cl | Tr 42 |
| 1 | 100 | 100 | 10 | 10 | 100 | 100 | 100 | 10 | 10 | 100 | 100 | 100 | 100 |
| 2(a) | 50 | — | 50 | 50 | 10 | 50 | 50 | 50 | 50 | 500 | 50 | 50 |
| 2(b) | 5 | 50 | 500 | 50 | 500 | 5 | 100 | 100 | 500 | 5 | 500 | 100 | 500 |
| 2(c) | 5 | 500 | 50 | 50 | 500 | 5 | 500 | 50 | 50 | 50 | 500 | 50 | 500 |

*Sa = S. aureus
Ec = E. coli
Ca = C albicans
Tm = T. mentagrophytes
An = A. niger
Bs = B. subtilis
Aa = A. aerogenes
Cp = C. pelliculosa
Pp = P. pullulans
St = S. typhosa
Ps 10 = Pseudomonas Sp. Strain 10
Cl = Ceratocystis IPS
Tr 42 = Trichoderm Sp. Madison P-42
— = not tested

DESCRIPTION OF SOME PREFERRED EMBODIMENTS

The following additional description and examples further describe the invention and the manner and process of making and using it to enable the art skilled to make and use the same and set forth the best mode contemplated by the inventor of carrying out the invention.

EXAMPLE 1—3-(2-Thiophenesulfonyl)-2-chloropropane nitrile

In a Fisher-Porter pressure reactor were placed 18.26 g (0.10 mol) of 2-thiophenesulfonyl chloride, 10.60 g (0.20 mol) of acrylonitrile, 2 g of acetonitrile, 0.130 g (1.0 mmol) of cupric chloride, and 0.210 g (1.5 mmol) of triethylamine hydrochloride. The contents of the tube were frozen in a solid carbon dioxide bath, then evacuated to a pressure of 2 mm Hg and sealed. The tube was then heated in an oil bath at 115° C. for 24 hours. The tube was allowed to cool, and the contents were transferred to a single-neck, round-bottom flask. The volatiles were removed in vacuo, leaving a heavy oil. A small amount of methanol was added thereto, and the resulting solution was cooled to give 10.55 g of crude product. The crude product was recrystallized from absolute ethanol to give 4.13 g of the title compound as small plates, mp 80°–82° C. A 4.00 g second crop, mp 78°–80° C., was also obtained.

Anal. Calculated for $C_7H_6ClNO_2S_2$: C, 35.67; H, 2.56; N, 5.94; S, 27.21. Found: C, 35.70; H, 2.64; N, 6.13; S, 27.40.

EXAMPLE 2—3-(5-Lower alkyl-2-thiophenesulfonyl)-2-chloropropanenitrile

The procedure of Example 1 was repeated, substituting (a) 5-methyl-, (b) 5-ethyl- and (c) 5-n-butyl-substituted-2-thiophenensulfonyl chloride in place of 2-thiophenesulfonyl chloride to obtain the corresponding homologs of Example 1. Their physical properties are summarized in the following Table:

TABLE II

| Compound of Example | M.p., °C. | Analysis Calculated | | | | Found | | | |
|---|---|---|---|---|---|---|---|---|---|
|  |  | C | H | N | Cl | C | H | N | Cl |
| 2(a) | 84 | 38.5 | 3.2 | 5.62 | 14.25 | 38.3 | 3.26 | 5.50 | 13.9 |
| 2(b) | 142–144 | — | 3.82 | 5.30 | — | — | 4.13 | 5.22 | — |
| 2(c) | 133 | — | 4.84 | 4.80 | 12.10 | — | 5.09 | 4.71 | 12.01 |

— = not determined

Preparation of Starting Materials

The 2-thiophenesulfonyl chlorides are prepared by the method disclosed in *Chemical Abstracts* 56:456f, German Pat. No. 1,088,509. The corresponding sulfonyl bromides are prepared by adding to a solution of methanol and hydrazine a 2-thiophenesulfonyl chloride at a reaction temperature between about 7° and about 15° C. to form the corresponding thiophenesulfonyl hydrazine, allowing the reaction mixture to warm to room temperature, removing the methanol in vacuo, recovering a mixture of a heavy oil and a solid, treating the mixture with water whereby the solid is dissolved and the oil is separated. Thereafter, the mixture of oil and water is mixed in a flask containing chloroform and a magnetic stirrer, crushed ice is added thereto and to the resulting slurry is added bromine to form the sulfonyl bromide, the bromine being added at such a rate that the reaction temperature remains below 10° C. After the addition of bromine is complete and the bromine color has dissipated, the layers are separated, the chloroform layer is dried over magnesium sulfate, and the chloroform removed in vacuo to leave a yellow oil which crystallizes on addition of hexane. The solid is filtered and dried to give the corresponding sulfonyl bromide in crystalline form.

What is claimed is:

1. A compound corresponding to the formula

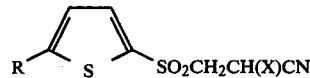

wherein R represents one of H, $C_{1-4}$ alkyl, Cl and Br and X represents Cl or Br.

2. The compound of claim 1 which is 3-(2-thiophenesulfonyl)-2-chloropropanenitrile.

3. The compound of claim 1 which is 3-(5-methyl-2-thiophenesulfonyl)-2-chloropropanenitrile.

4. The compound of claim 1 which is 3-(5-ethyl-2-thiophenesulfonyl)-2-chloropropanenitrile.

5. The compound of claim 1 which is 3-(5-n-butyl-2-thiophenesulfonyl)-2-chloropropanenitrile.

* * * * *